US008316898B2

(12) United States Patent
Zinger et al.

(10) Patent No.: US 8,316,898 B2
(45) Date of Patent: Nov. 27, 2012

(54) AUTOMATIC LIQUID DRUG PREPARATION APPARATUS FOR THE PREPARATION OF A PREDETERMINED DOSAGE OF LIQUID DRUG

(75) Inventors: Freddy Zinger, Ra'anana (IL); Igor Denenburg, Riga District (LV); Amir Lev, Kfar Saba (IL)

(73) Assignee: Medimop Medical Projects Ltd., Ra'anana (IL)

( * ) Notice: Subject to any disclaimer, the term of this patent is extended or adjusted under 35 U.S.C. 154(b) by 601 days.

(21) Appl. No.: 12/598,469

(22) PCT Filed: May 4, 2008

(86) PCT No.: PCT/IL2008/000606
§ 371 (c)(1),
(2), (4) Date: Nov. 2, 2009

(87) PCT Pub. No.: WO2008/135989
PCT Pub. Date: Nov. 13, 2008

(65) Prior Publication Data
US 2010/0087786 A1    Apr. 8, 2010

(30) Foreign Application Priority Data
May 2, 2007    (IL) ........................................ 182922

(51) Int. Cl.
*B65B 1/04*    (2006.01)
(52) U.S. Cl. ............................ 141/27; 604/224; 604/246
(58) Field of Classification Search .................... 141/27, 141/97, 192, 198, 319, 329, 330; 604/224, 604/246
See application file for complete search history.

(56) References Cited

U.S. PATENT DOCUMENTS 4,534,758 A    8/1985 Akers et al.
6,162,199 A *  12/2000 Geringer ....................... 604/208
(Continued)

FOREIGN PATENT DOCUMENTS
DE    4314657 A1    11/1994
(Continued)

OTHER PUBLICATIONS

International Search Report dated Mar. 30, 2011 in Int'l Application No. PCT/IL2010/000939.

(Continued)

*Primary Examiner* — Timothy L Maust
*Assistant Examiner* — Robert Bell, III
(74) *Attorney, Agent, or Firm* — Panitch Schwarze Belisario & Nadel LLP

(57) ABSTRACT

Automatic liquid drug preparation apparatus for preparing a liquid drug assemblage with a predetermined dosage of liquid drug. The liquid drug assemblage is prepared from a preparatory assemblage including a fluid control device having a body member with a syringe port, a vial adapter, and an administration port, a vial pre-filled with powder or liquid medicament, and a syringe pre-filled with diluent for mixing with the medicament. The automatic liquid drug preparation apparatus includes a housing, a cradle for receiving the preparatory assemblage, and a controller for controlling a motorized syringe drive unit for selectively transferring liquid contents between the syringe and the vial, a motorized cradle drive unit for selectively rotating the cradle relative to the housing, and a motorized vial adapter release unit for selectively detaching the vial adapter with its attached spent vial from the body member to form the liquid drug assemblage.

14 Claims, 18 Drawing Sheets

U.S. PATENT DOCUMENTS

| | | |
|---|---|---|
| 6,238,372 B1 | 5/2001 | Zinger et al. |
| 6,581,648 B1 * | 6/2003 | Zolentroff et al. ............... 141/2 |
| 7,500,961 B2 * | 3/2009 | Nemoto .................... 604/151 |
| 7,703,483 B2 * | 4/2010 | Hartman et al. ............... 141/27 |
| 7,914,499 B2 | 3/2011 | Gonnelli et al. |
| 2004/0162515 A1 | 8/2004 | Chornenky et al. |
| 2006/0049209 A1 | 3/2006 | Baker |
| 2006/0169348 A1 * | 8/2006 | Yigal ............................ 141/21 |
| 2006/0224105 A1 | 10/2006 | Thorne et al. |

FOREIGN PATENT DOCUMENTS

| | | |
|---|---|---|
| WO | 96/29113 A1 | 9/1996 |
| WO | 2006124634 A1 | 11/2006 |
| WO | 2007/079305 A2 | 7/2007 |
| WO | 2007/130809 A2 | 11/2007 |
| WO | 2008135989 A1 | 11/2008 |

OTHER PUBLICATIONS

International Search Report dated May 4, 2011 in Int'l Application No. PCT/IL2010/001077.

International Search Report Issued Aug. 28, 2010 in Int'l Application No. PCT/IP2008/000606.

Notice of Intention to Grant EP Application No. 08738307.1.

U.S. Appl. No. 13/518,036 by Lev, filed Jun. 21, 2012.

International Search Report Issued Aug. 28, 2008 in Int'l Application No. PCT/IP2008/000606.

International Search Report Issued Aug. 28, 2008 in Int'l Application No. PCT/IL2008/000606.

* cited by examiner

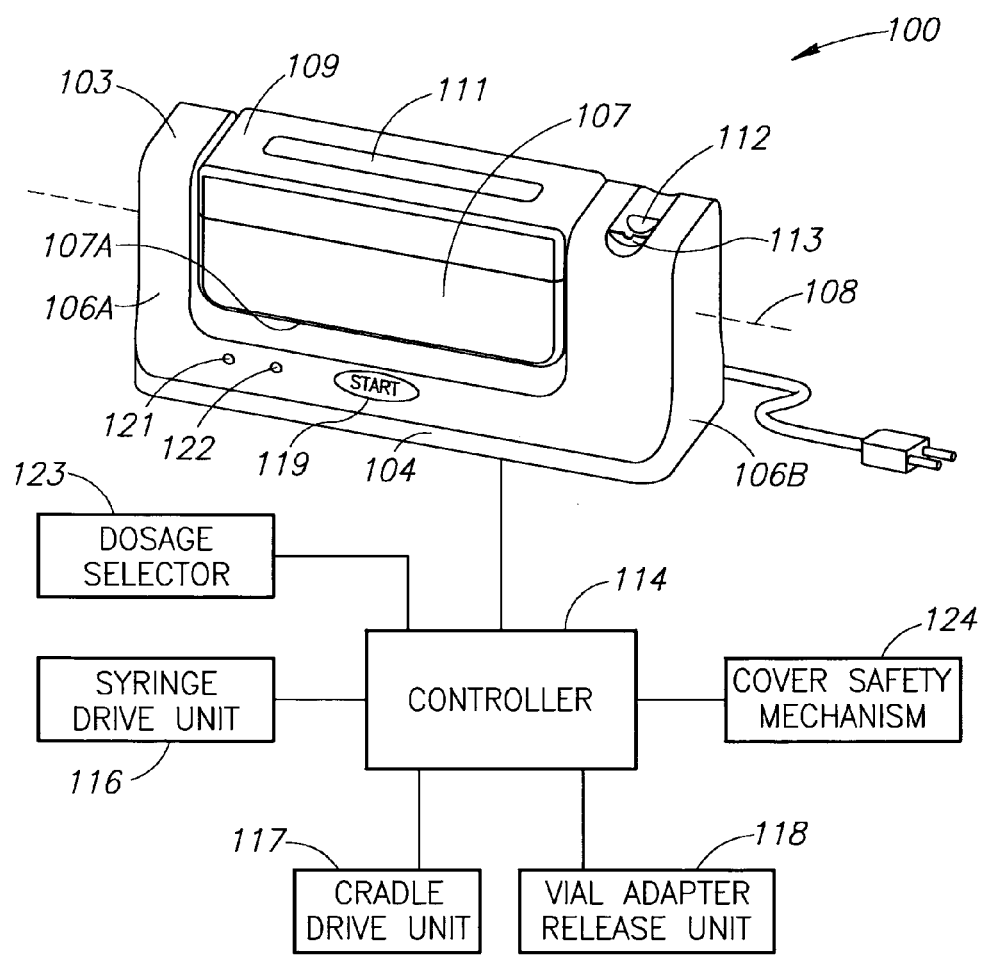
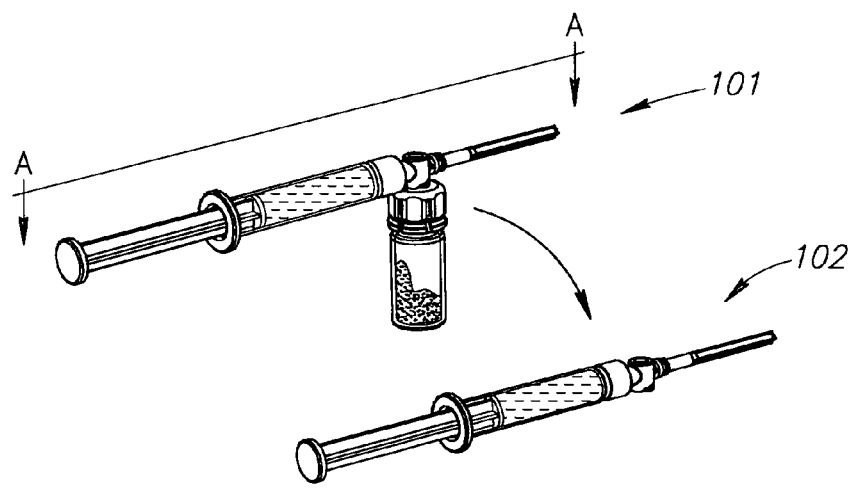
FIG.1

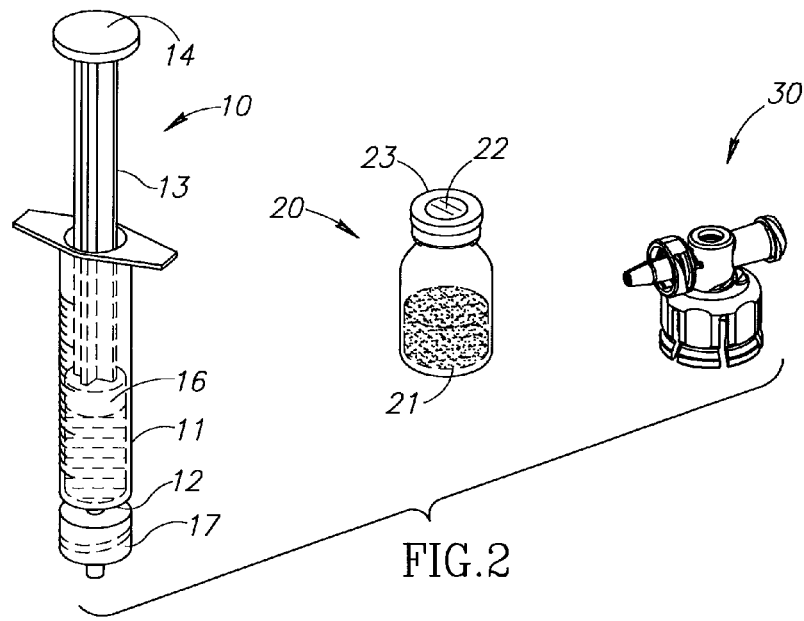
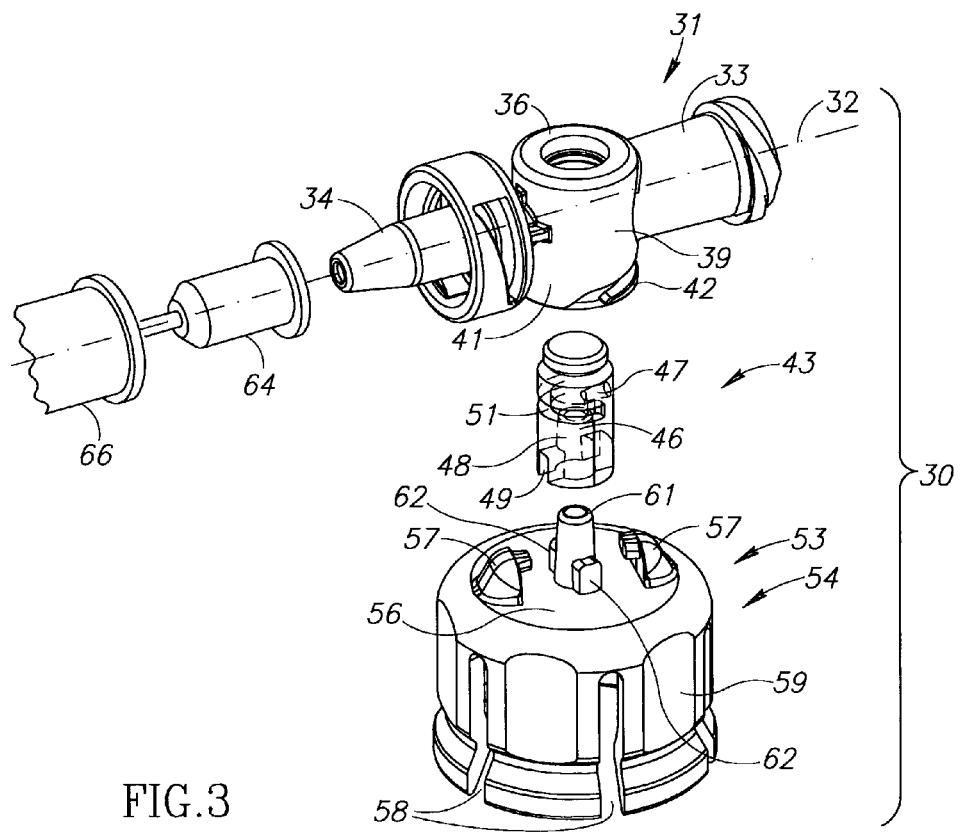

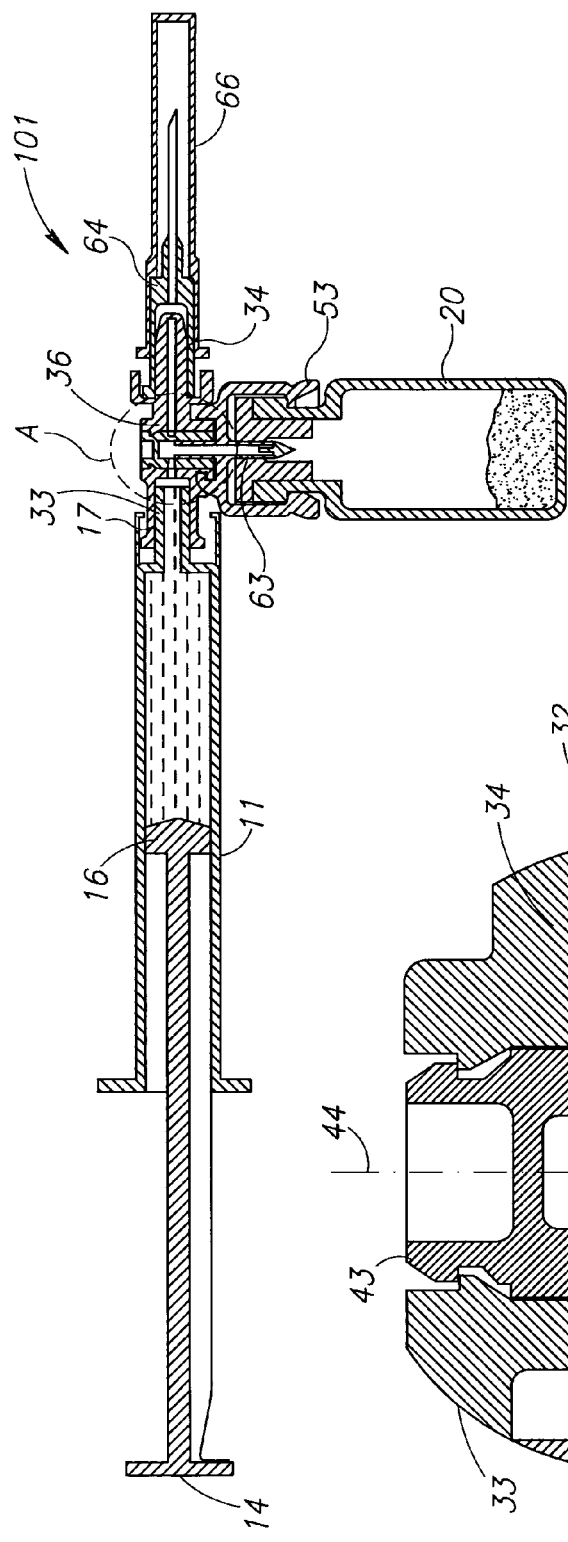
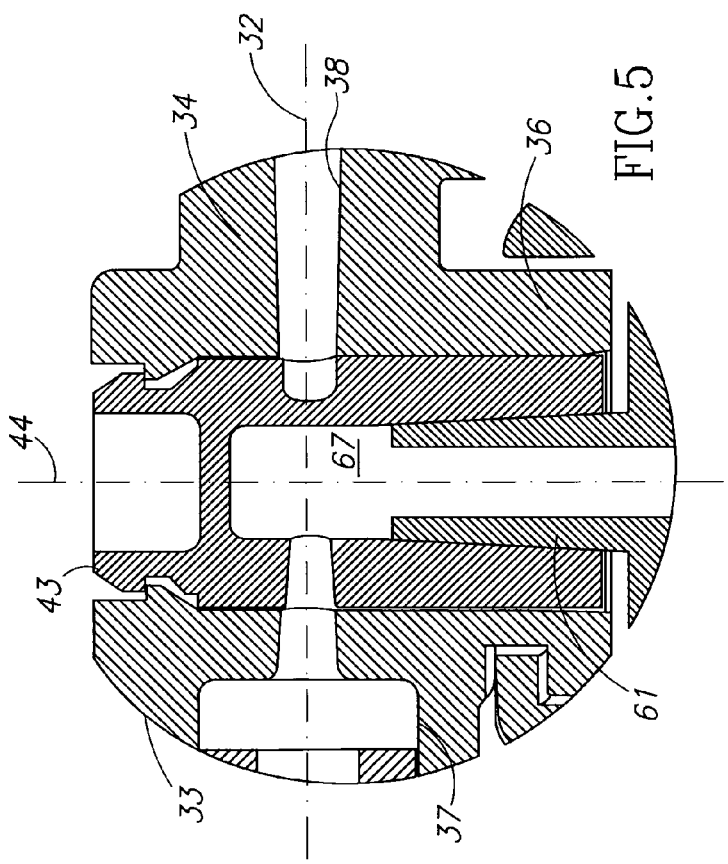
FIG. 4
FIG. 5

AUTOMATIC LIQUID DRUG PREPARATION APPARATUS FOR THE PREPARATION OF A PREDETERMINED DOSAGE OF LIQUID DRUG

CROSS-REFERENCE TO RELATED APPLICATION

This application is a section 371 of International Application No. PCT/IL2008/000606, filed May 4, 2008, which was published in the English language on Nov. 13, 2008 under International Publication No. WO 2008/135989 A1 and the disclosure of which is incorporated herein by reference.

FIELD OF THE INVENTION

The invention pertains to the preparation of predetermined dosages of liquid drug for administration purposes.

BACKGROUND OF THE INVENTION

Commonly owned U.S. Pat. No. 6,238,372 to Zinger et al., the contents of which are incorporated herein by reference, illustrates and describes fluid control devices for the preparation of liquid drugs for administration purposes. US '372 FIGS. 1 to 19 illustrate fluid control devices including a housing with a syringe port for receiving a syringe pre-filled with diluent with or without an active chemical component, a vial adapter port with a vial adapter for snap fitting onto a vial pre-filled with powder or liquid medicament, and a drug administration port for administering a liquid drug. The fluid control devices include a rotatable flow member for providing either a mixing flow path between the syringe port and the vial adapter or an administration flow path between the syringe port and the drug administration port. US '372 FIGS. 11 to 15 illustrate fluid control devices having vial adapter ports with vial adapters intended to be rotationally detached after a mixing procedure whereupon a detached vial adapters is intended to be discarded together with its attached spent vial. Such fluid control devices are commercially available under the registered trademark MIXJECT® from Medimop Medical Projects Ltd., Ra'anana, Israel. MIXJECT® product information is available at http://www.westpharma.com/products/medimop/Information/mixject.pdf.

For the sake of convenience, the following two terms are employed hereinafter in the specification and claims: "Preparatory assemblage" referring to a MIXJECT® fluid control device with its vial adapter and an attached vial pre-filled with powder or liquid medicament and a syringe pre-filled with diluent for mixing with the medicament, and "liquid drug assemblage" referring to the preparatory assemblage with its syringe filled with a predetermined dosage of liquid drug and without its detached vial adapter and attached spent vial. The liquid drug assemblages are typically inserted into auto-injectors for administering their entire liquid drug contents. The instructions of use for a MIXJECT® fluid control device for processing a preparatory assemblage into a liquid drug assemblage are as follows:

Step 1: User snap fits a fluid control device's vial adapter onto a vial pre-filled with powder or liquid medicament.

Step 2: User inserts a syringe pre-filled with diluent into the syringe port to form the preparatory assemblage.

Step 3: User injects the diluent into the vial.

Step 4: User agitates the preparatory assemblage to mix the diluent with the medicament to form the liquid drug.

Step 5: User inverts the preparatory assemblage.

Step 6: User aspirates the liquid drug into the preparatory assemblage.

Step 7: User rotates the vial adapter to remove same and attached spent vial to convert the preparatory assemblage into the liquid drug assemblage.

Step 8: In the case of certain liquid drugs, user ejects some liquid drug contents to leave a predetermined dosage of liquid drug for administration purposes.

It has now been found that some users have encountered difficulties in manually processing preparatory assemblages into liquid drug assemblages as now explained. Pre-filled syringes typically include air with their diluent contents which often leads to the presence of one or more air bubbles in a liquid drug assemblage's liquid drug contents thereby burdening users to remove same prior to administration. Exemplary relative volumes of diluent and air in 1 ml pre-filled syringes include 1.2 ml diluent and 0.4 ml air. In cases of liquid drug assemblage's liquid drug contents containing some air bubbles, users typically hold a liquid drug assemblage upright with its needle facing upwards and flick on the syringe's barrel to break up any air bubbles into smaller air bubbles at the top of its syringe which they then eject. However, it should be noted that some freshly mixed liquid drug contents start bubbling in a liquid drug assemblage after a certain length of time due to a chemical reaction between a medicament and a diluent including an active chemical component, thereby re-introducing air bubbles into the liquid drug contents.

Some users may inadvertently cause foaming of a liquid drug thereby requiring a long settling period before the processing of a preparatory assemblage can be finalized and its liquid drug contents is suitable for administration. Such foaming can be caused by injecting diluent into a vial too quickly or agitating a preparatory assemblage too violently. Conversely, particularly in the case of a powder medicament, insufficient agitation may lead to some of a vial's contents not being dissolved. Additionally, some users occasionally inadvertently aspirate an insufficient volume of liquid drug prior to detachment of a vial adapter which is typically detrimental to an intended medical treatment.

Some syringes have graduations which are semi-circular and, depending on the Luer connection between a syringe and a MIXJECT® fluid control device, can face downwards when a preparatory assemblage is inverted to aspirate liquid drug contents thereinto such that a user cannot see them. Moreover, some users have difficulty reading a syringe's graduations to accurately determine its volume of liquid drug.

SUMMARY OF THE INVENTION

The present invention is for automatic liquid drug preparation apparatus for processing a preparatory assemblage with liquid drug constituents into a liquid drug assemblage with a predetermined dosage of liquid drug. The apparatus includes a housing, a cradle for manual insertion of a preparatory assemblage thereinto, and a controller for controlling a motorized syringe drive unit, a motorized cradle drive unit, and a motorized vial adapter release unit according to a predetermined sequence of steps.

The motorized syringe drive unit is employed for selectively transferring liquid contents between a syringe and a vial. The motorized cradle drive unit is employed for selectively rotating the cradle with the preparatory assemblage relative to the housing. The motorized vial adapter release unit is employed for selectively detaching a vial adapter with its attached spent vial from a preparatory assemblage to form a liquid drug assemblage. The motorized drive units each preferably include a dedicated motor. Alternatively, two or all three drive units may be driven by a single motor.

The controller executes a syringe linear encoder reset procedure for resetting a syringe linear encoder for determining the location of a syringe's plunger relative to the syringe's barrel for ensuring accurate aspirations of a predetermined dosage of liquid drug. The controller executes a trapped air displacement procedure for progressively displacing substantially most of any air entrapped in a preparatory assemblage's mixing flow path into the vial thereby leaving a liquid drug assemblage with air free liquid drug contents except in some instances in which the liquid drug contents include an accumulated air bubble volume of minute air bubbles of several few micro liters. The automatic liquid drug preparation apparatus affords proper mixing of diluent with a vial's entire medicament contents without substantial foaming, and accurate aspiration of a predetermined dosage of liquid drug for administration to a patient. Visual indications and/or audio-visual indications can be employed for indicating the status of the operation of the apparatus.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 1 shows pictorial representations of a preparatory assemblage and a liquid drug assemblage and a combined pictorial representation and block diagram of an automatic liquid drug preparation apparatus for processing the preparatory assemblage into the liquid drug assemblage;

FIG. 2 shows pictorial representations of a syringe, a vial, and a fluid control device according to U.S. Pat. No. 6,238,372's 11 to 15;

FIG. 3 shows an exploded view of FIG. 2's fluid control device;

FIG. 4 is longitudinal cross section of a preparatory assemblage along line A-A in FIG. 1;

FIG. 5 is a close-up of the section of the preparatory assemblage denoted A in FIG. 4;

DETAILED DESCRIPTION OF PREFERRED EMBODIMENTS OF THE PRESENT INVENTION

Figure 6:
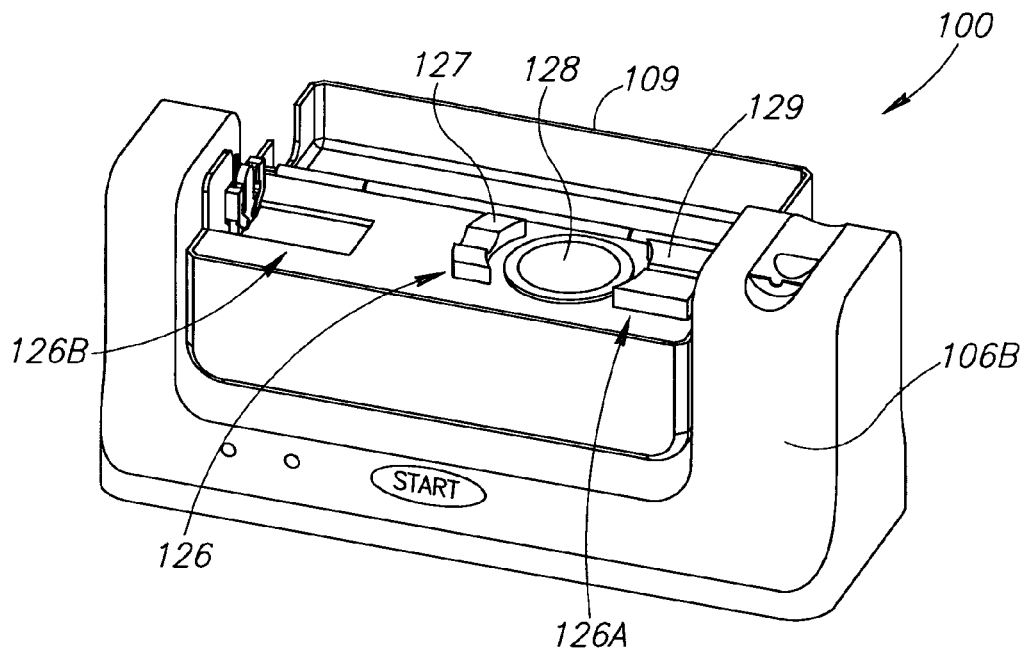
FIG. 6 is a pictorial representation of the automatic liquid drug preparation apparatus with an upright cradle and an open hinged cover.

FIG. 1 shows an automatic liquid drug preparation apparatus 100 for use with a preparatory assemblage 101 for preparing a liquid drug assemblage 102 with a predetermined dosage of liquid drug for administration purposes. The apparatus 100 can be mains or battery operated and includes a housing 103 for placing on a horizontal surface. The housing 103 includes a horizontal base member 104 and a pair of spaced apart upright end pieces 106A and 106B. The preparatory assemblage 101 is manually inserted into a box-shaped cradle 107 with a bottom surface 107A. The end pieces 106A and 106B rotatably support the cradle 107 about a horizontal axis of rotation 108. The cradle 107 includes a hinged cover 109 for securing the preparatory assemblage 101 therein. The cover 109 includes a transparent window 111 for enabling a user to view the operation of the apparatus 100. The end piece 106B is formed with a blind bore 112 for insertion of a vial for assisting a user to assemble the preparatory assemblage 101. The end piece 106B is also formed with a V-shaped opener 113 for assisting a user to remove a needle shield from a liquid drug assemblage 102 including a needle with a needle shield.

The apparatus 100 includes a controller 114 for controlling the operation of a motorized syringe drive unit 116, a motorized cradle drive unit 117, and a motorized vial adapter release unit 118. The apparatus 100 includes a START pushbutton 119 for initiating operation, a green LED 121 for indicating a correct condition, and a red LED 122 for indicating an error condition preventing operation. The apparatus 100 includes a dosage selector 123 for selecting a dosage of liquid drug to be aspirated into the liquid drug assemblage 102. The apparatus 100 also includes a cover safety mechanism 124 for preventing operation of the apparatus 100 in the event the cover 109 is not fully closed.

FIG. 2 shows a syringe 10, a vial 20, and a fluid control device 30. The syringe 10 includes a barrel 11 with an end wall 12, a plunger 13 with a plunger head 14 and an elastomer plunger tip 16 for sealing the barrel 11, and a male Luer lock connector 17. The vial 20 includes an opened topped bottle 21 sealed by a rubber stopper 22 capped by a metal band 23. The vial 20 includes powder or liquid medicament. The syringe 10 is pre-filled with a diluent for mixing with the vial 20's medicament.

FIGS. 3 to 5 show the fluid control device 30 includes a body member 31 having a longitudinal axis 32, a syringe port 33 and a drug administration port 34 co-directional with the longitudinal axis 32, and a tubular vial adapter port 36 intermediate the syringe port 33 and the drug administration port 34. The syringe port 33 includes a lumen 37 in flow communication with the vial adapter port 36 and slidingly receiving the syringe 10. The drug administration port 34 includes a lumen 38 in flow communication with the vial adapter port 36 and intended for administrating a liquid drug.

The vial adapter port 36 has an outer cylindrical surface 39 with a lowermost portion 41 having a pair of opposite quarter turn screw threads 42. The vial adapter port 36 supports a flow control member 43 rotatable about an axis of rotation 44 generally perpendicular to the longitudinal axis 32. The flow control member 43 has an L-shaped mixing flow channel 46 including a radial section 47 for registration with the syringe port's lumen 37 in a mixing flow control position and an axial section 48 terminating in a diametrical slot 49. The flow control member 43 has a peripheral semi-circular administration flow channel 51 for registration with the syringe port's lumen 37 and the drug administration port's lumen 38 in an administration flow control position subsequent to a quarter turn with respect to its mixing flow control position.

The fluid control device 30 includes a vial adapter 53 with a downward depending skirt 54 for telescopically receiving the vial 20. The skirt 54 has a top surface 56 with a pair of opposite screw thread members 57 for screw thread engaging the screw threads 42 thereby coupling the vial adapter 53 to the body member 31, and six upright slits 58 for forming downward depending flex members 59 for snap fitting onto the vial 20. The vial adapter 53 includes an upright tapered hollow male connector 61 for sealing insertion into the flow control member's axial section 48 and a pair of keys 62 for insertion into the flow control member's slot 49 for coupling the vial adapter 53 to the flow control member 43. The vial adapter 53 includes a downward depending hollow pointed cannula 63 for puncturing a vial's rubber stopper 22 and extending into a vial bottle 21's interior. The male connector 61 and the cannula 63 are in flow communication. The drug administration port 34 is preferably fitted with a needle 64 protected by a needle shield 66 to prevent needle stick injuries. The fluid control device 30 includes a mixing flow path 67 extending between the syringe port 33 and the vial adapter port 36 in the flow control member 43's mixing flow control position.

FIG. 6 shows the cradle 107 has a top surface 126 with a leading end 126A and a slotted trailing end 126B relative to the end piece 106B. The leading end 126A includes a trailing grooved support member 127, an aperture 128 and a leading grooved support member 129. The preparatory assemblage 101 is longitudinally aligned on manual insertion into the cradle 107 such that its barrel 11 rests on the support member 127, its vial adapter 53 with attached vial 20 are inserted into the aperture 128 and its needle shield 66 rests on the support member 129.

Figure 7:
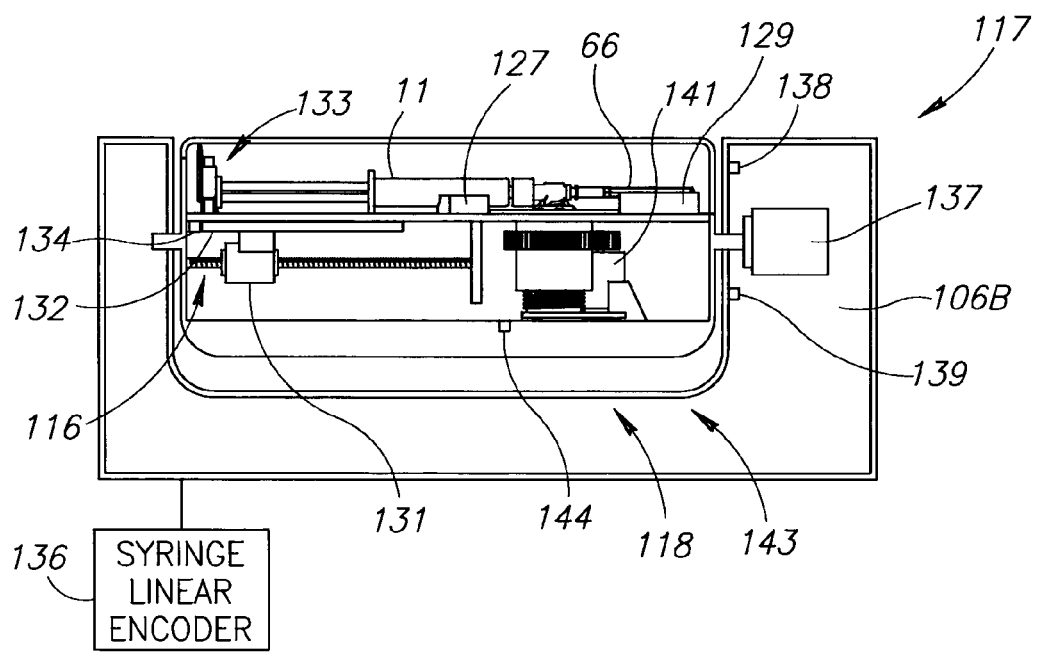
FIG. 7 is a schematic longitudinal cross section of the automatic liquid drug preparation apparatus.

FIG. 7 shows the syringe drive unit 116 includes a motor 131 for reciprocating a carriage 132 having a plunger head drive member 133 for reciprocating a plunger head 14. The plunger head drive member 133 is preferably designed such that the same automatic liquid drug preparation apparatus 100 can used with syringes containing different volumes of diluent and therefore having their plungers 13 at different initial positions relative to their barrels 11. Such plunger head drive members 133 also compensate for component tolerances, assembly tolerances, and the like. The syringe drive unit 116 includes a micro-switch 134 corresponding to a home position of the plunger head drive member 133 at its remotest position from the end piece 106B thereby enabling insertion of a preparatory assemblage 101 with a syringe 10 pre-filled with a maximum volume of diluent. The controller 114 executes a syringe linear encoder reset procedure to reset a syringe linear encoder 136 for determining the location of the plunger 13 relative to the syringe's barrel 11 for compensating for assembly tolerances, component tolerances, and the like. The syringe linear encoder 136 is set to zero when the plunger tip 16 abuts against the inside surface of the syringe's end wall 12.

The cradle drive unit 117 includes a motor 137 for rotating the cradle 107 about its axis of rotation 108 between a micro-switch 138 for stopping the cradle 107 at an initial upright position and a micro-switch 139 for stopping the cradle 107 at an inverted position.

The vial adapter release unit 118 includes a motor 141 for rotating an annular vial adapter gripper 142 (described below with reference to FIGS. 12 to 14) for encircling the vial adapter 53 on manual insertion of the preparatory assemblage 101 in the cradle 107 and for gripping same. The vial adapter release member unit 118 also includes a vial adapter release mechanism 143 for selectively raising a vial adapter 53 and its attached spent vial for assisting a user to manually remove same from the cradle 107 and a micro-switch 144 for detecting the vial adapter release mechanism 143 at its lowermost position for enabling insertion of the preparatory assemblage 101 into the cradle 107.

Figure 8:
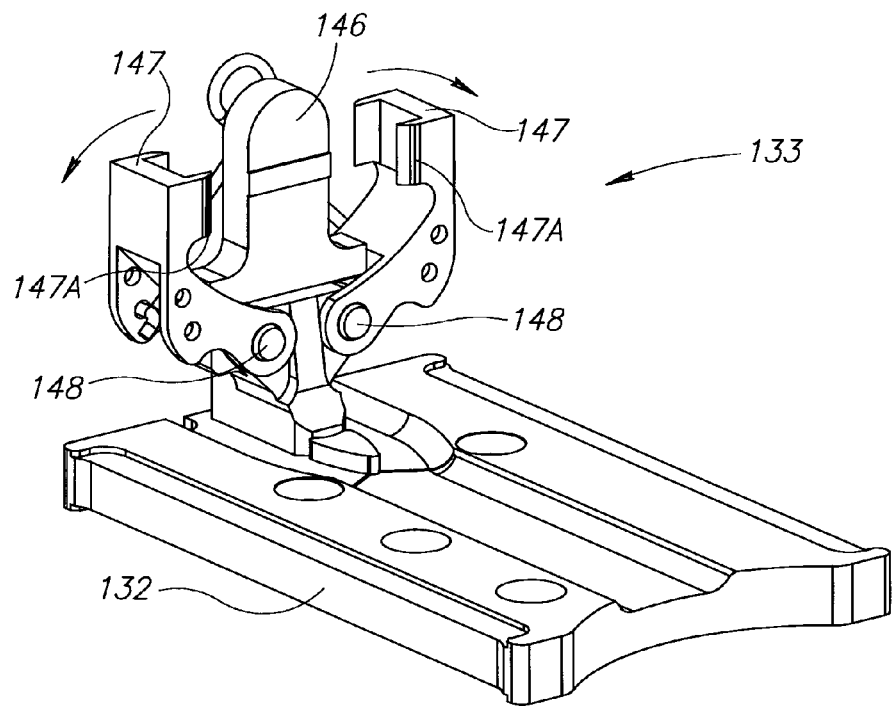
FIG. 8 is a front pictorial representation of a plunger head drive member for snap fitting onto a syringe's plunger head.
Figure 9:
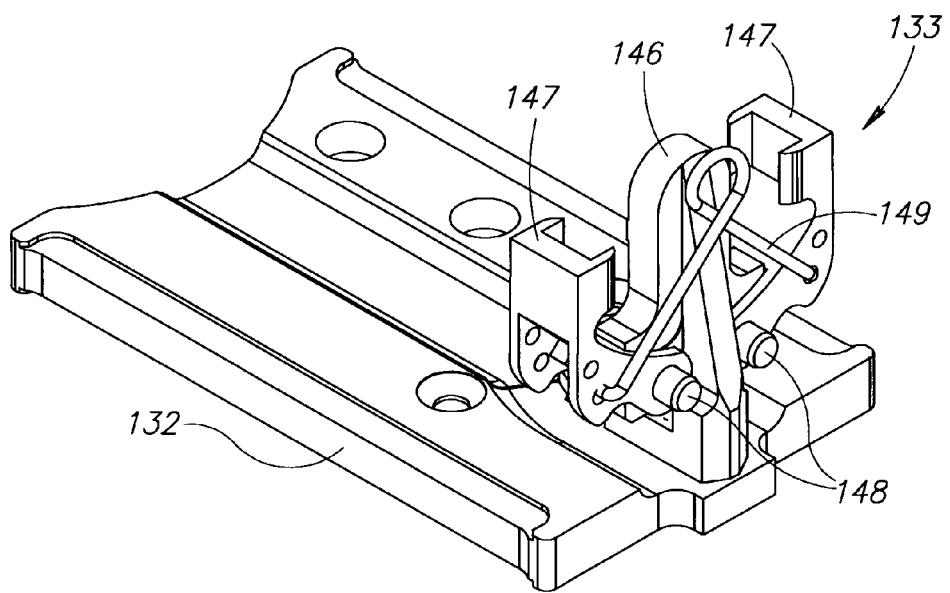
FIG. 9 is a rear pictorial representation of FIG. 8's plunger head drive member.
Figure 10:
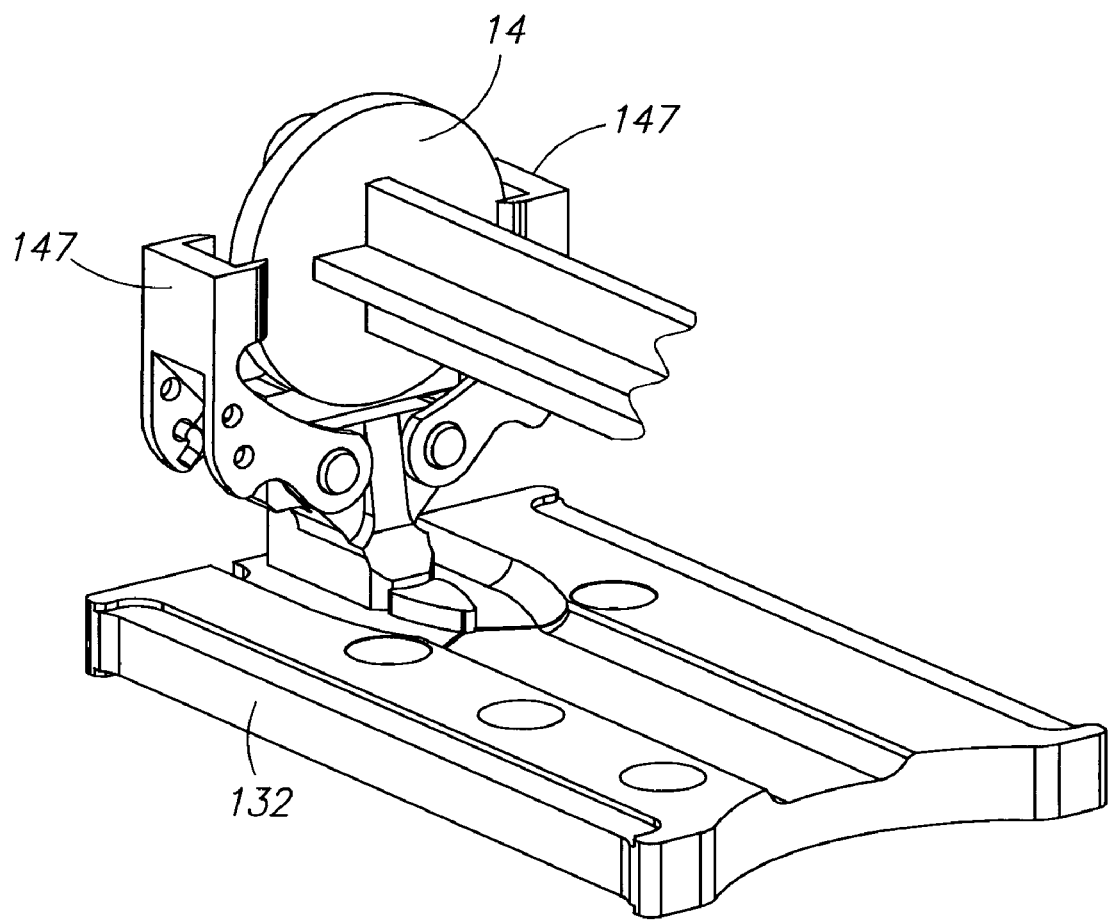
FIG. 10 is a front pictorial representation of FIG. 8's plunger head drive member snapped fitted onto a syringe's plunger head.

FIGS. 8 to 10 show the plunger head drive member 133 is preferably constituted by a flipper arrangement including a central rigid upright support member 146, a pair of flippers 147 pivotal on axles 148 co-directional with axis of rotation 108 and biased towards one another by a spring 149. The flippers 147 have inclined front surfaces 147A facing the end piece 106B for acting as cam surfaces for outwardly pivoting the flippers 147 relative to the support member 146 on application of sufficient force to overcome the spring 149 whereupon the flippers 147 snap onto the plunger head 14.

Figure 11A:
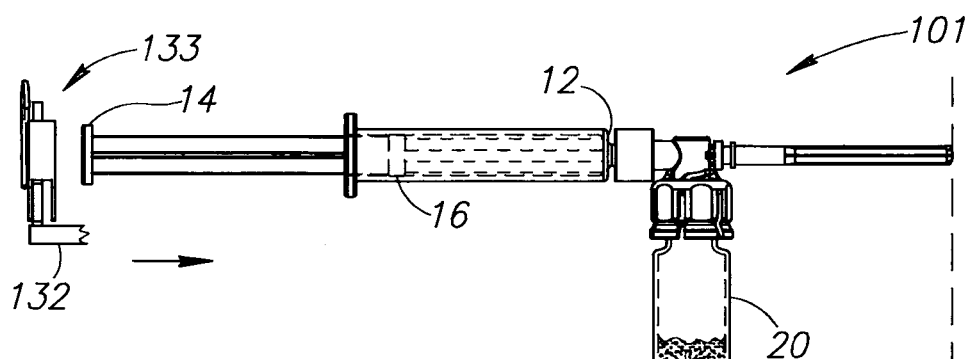
FIGS. 11A to 11D are pictorial representations showing the operation of FIG. 8's plunger head drive member.
Figure 11B:
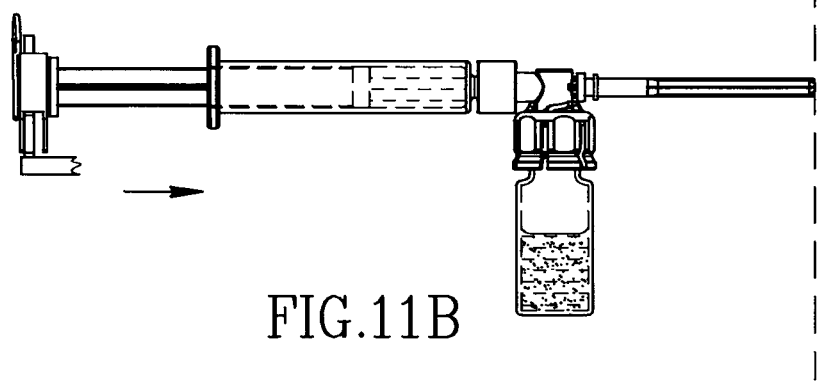
Figure 11C:
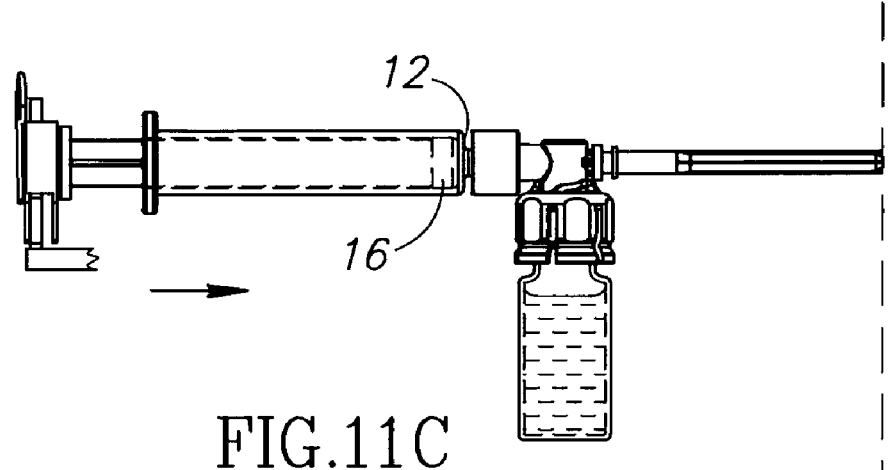
Figure 11D:
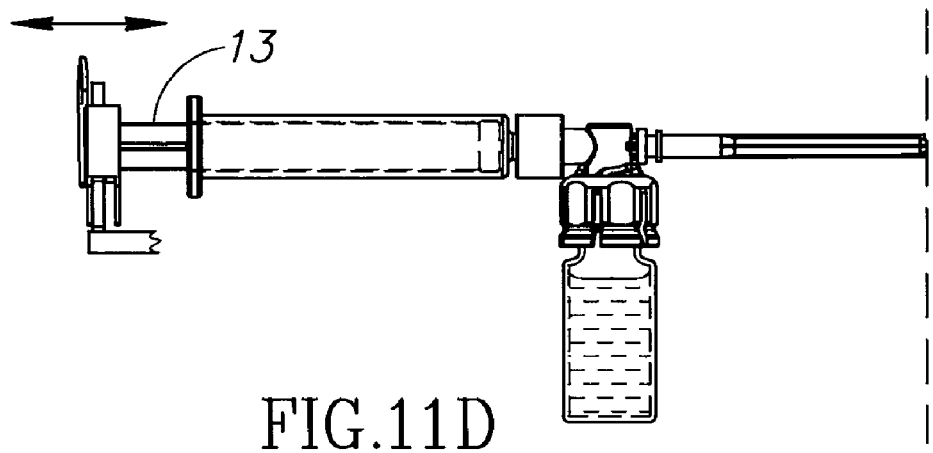

FIGS. 11A and 11B show the operation of the syringe drive unit 116 from its initial home position for urging the carriage 132 for injecting the syringe's diluent into the vial 20. Continued operation of the syringe drive unit 116 moves the flippers 147 to urge the plunger tip 16 towards the syringe's end wall 12 until the plunger tip 16 abuts thereagainst (see FIG. 11C) whereupon the plunger head 14 acts to urge the flippers 147 outwardly to their outward positions as indicated by the arrows in FIG. 8. Continued operation of the syringe drive unit 116 moves the flippers 147 forward to snap onto the plunger head 14 (see FIG. 11D) thereby enabling the syringe drive unit 116 to reciprocate the plunger 13.

Figure 12:
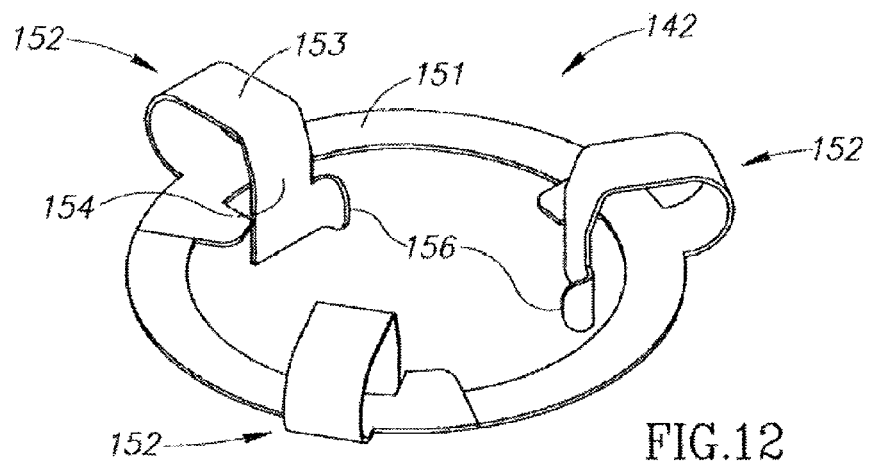
FIG. 12 is a pictorial representation of an annular vial adapter gripper with three leaf springs each having a tab for snap fit insertion into a vial adapter's alternate slits on manual insertion of a preparatory assemblage into the cradle.
Figure 13:
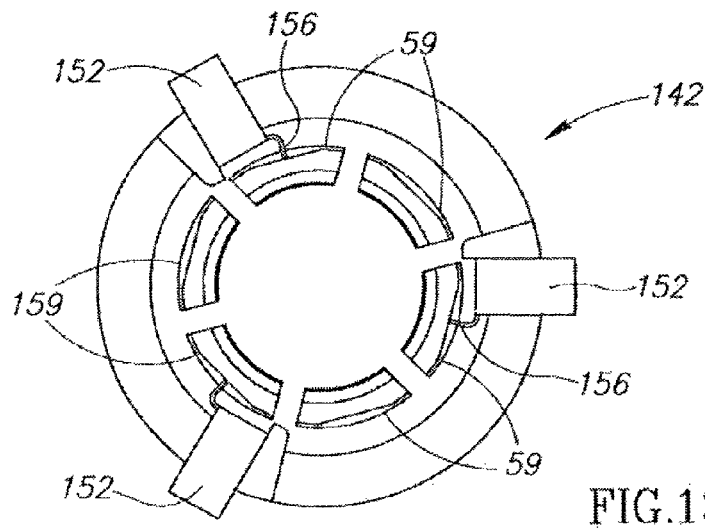
FIG. 13 is a pictorial representation showing FIG. 12's vial adapter gripper with its three leaf springs and their tabs urged against a vial adapter's alternate flex members.
Figure 14:
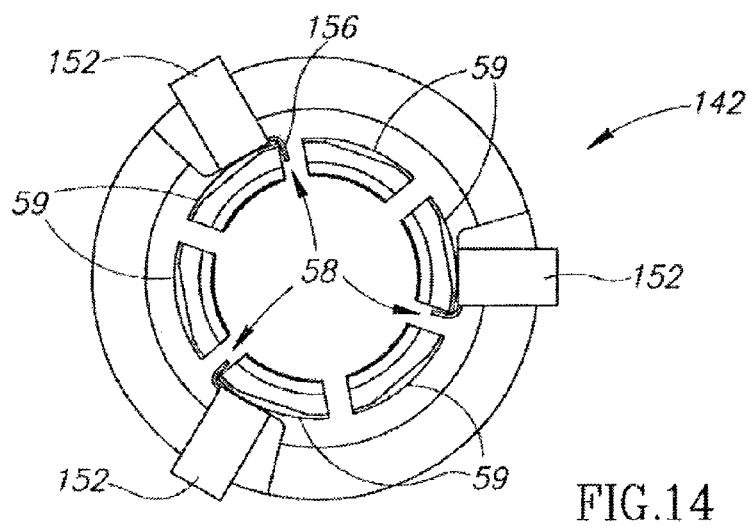
FIG. 14 is a pictorial representation showing FIG. 12's vial adapter gripper with its three leaf springs and their tabs inserted into a vial adapter's alternate slits.

FIG. 12 shows the vial adapter gripper 142 includes a ring 151 with preferably three equi-distanced leaf springs 152 in their non-flexed positions. The leaf springs 152 each have an inverted L-shaped with a horizontal section 153 flexibly connected to the ring 151 and an upright section 154 flexibly connected to the horizontal section 153 and inward of the ring 151. The upright sections 154 are each provided with a radial inwardly protruding tab 156 for snap fit insertion into a vial adapter's upright slit 58. FIG. 13 shows the vial adapter gripper 142 with its tabs 156 urged against alternate flex members 59 thereby outwardly flexing the leaf springs 152 relative to their non-flexed positions. FIG. 14 shows the vial adapter gripper 142 gripping a vial adapter 53 on rotation of the vial adapter gripper 142 relative to its FIG. 13's position for enabling the tabs 156 to snap fit into alternate slits 58 thereby enabling the vial adapter release unit 118 to rotate the vial adapter gripper 142 to detach a vial adapter 53.

Figure 15A:
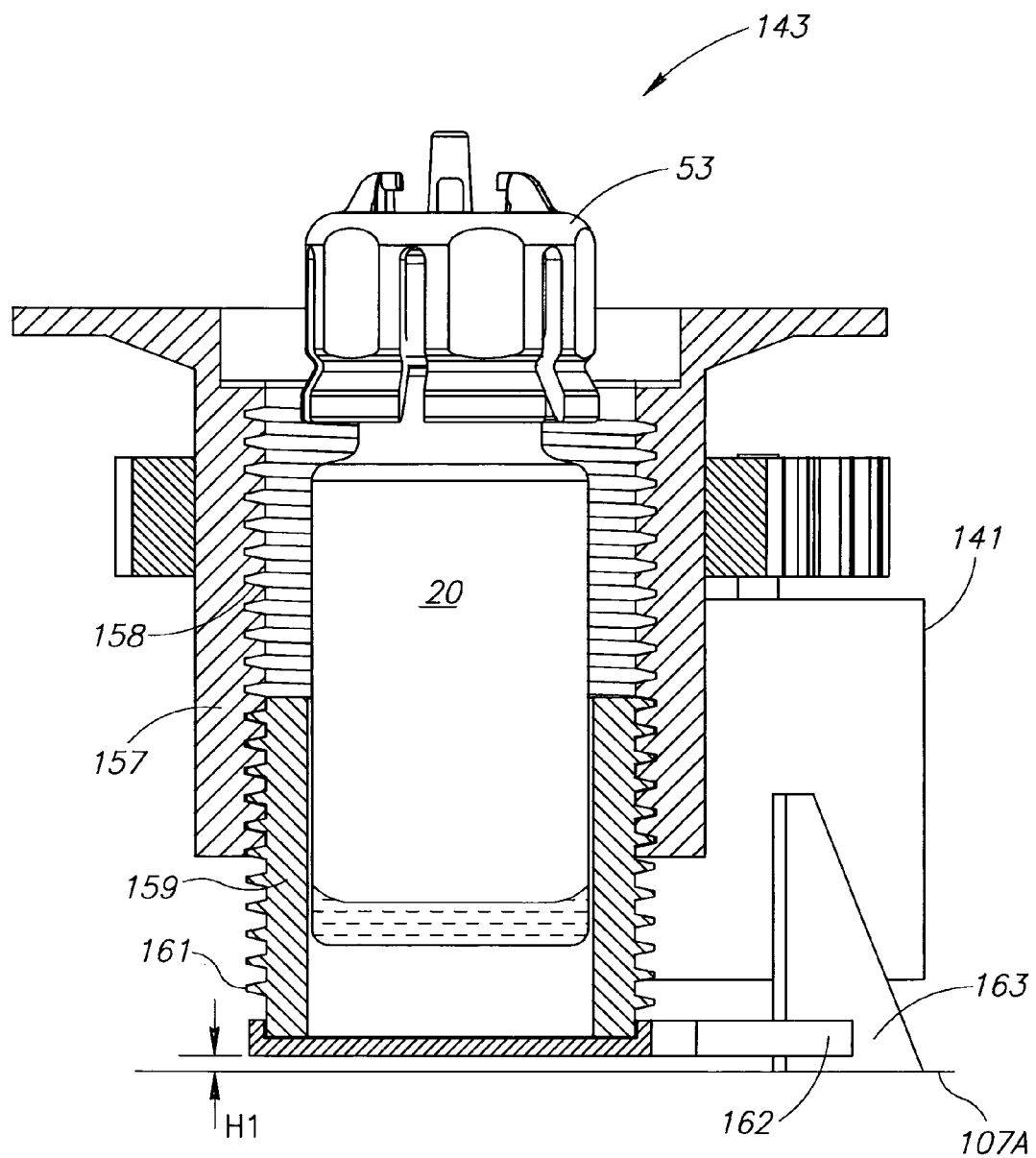
FIGS. 15A to 15C are pictorial representations showing three operative positions of a vial adapter release mechanism for selectively raising a vial adapter and its attached spent vial on detachment of a vial adapter from its fluid control device.
Figure 15B:
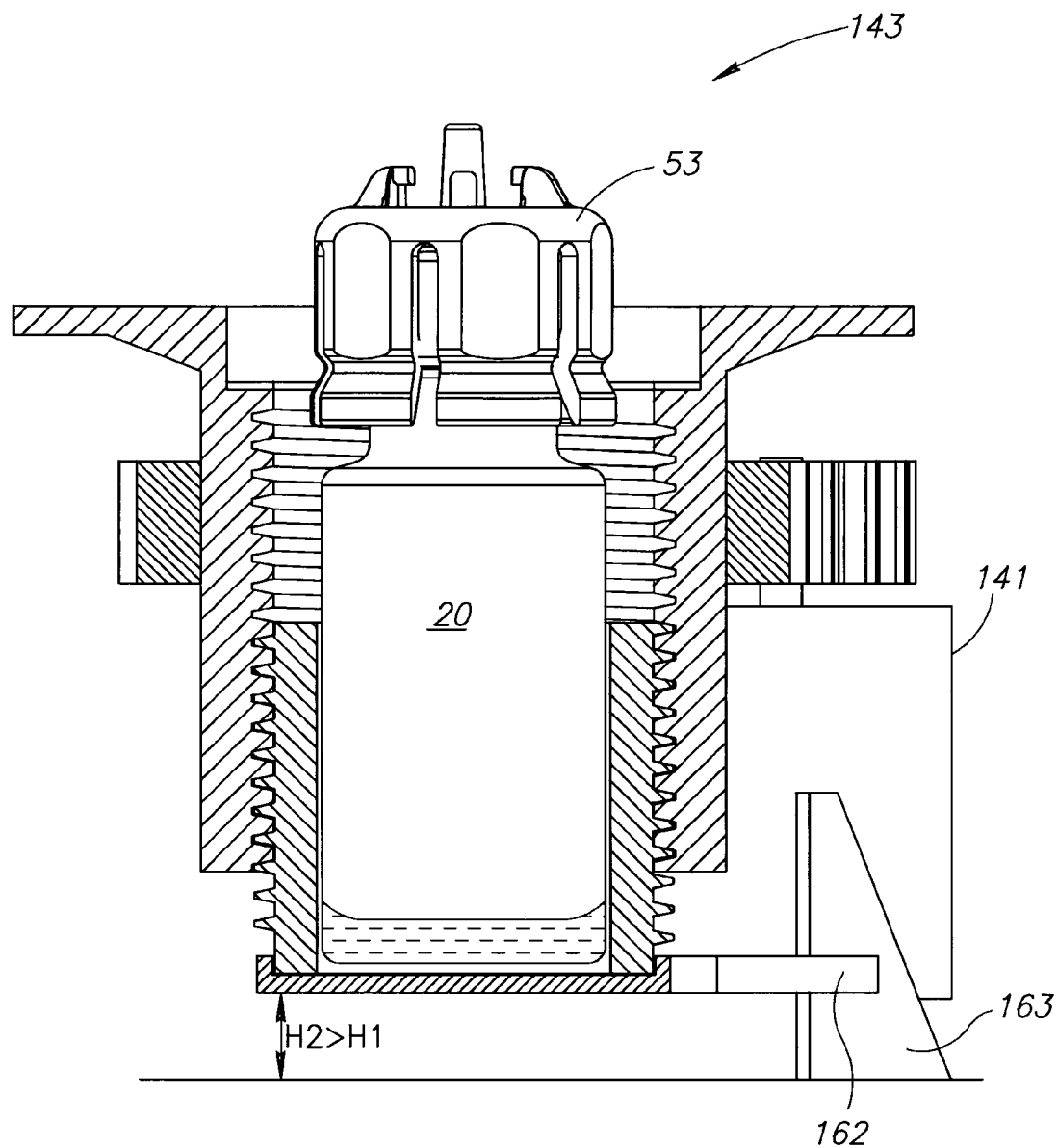
Figure 15C:
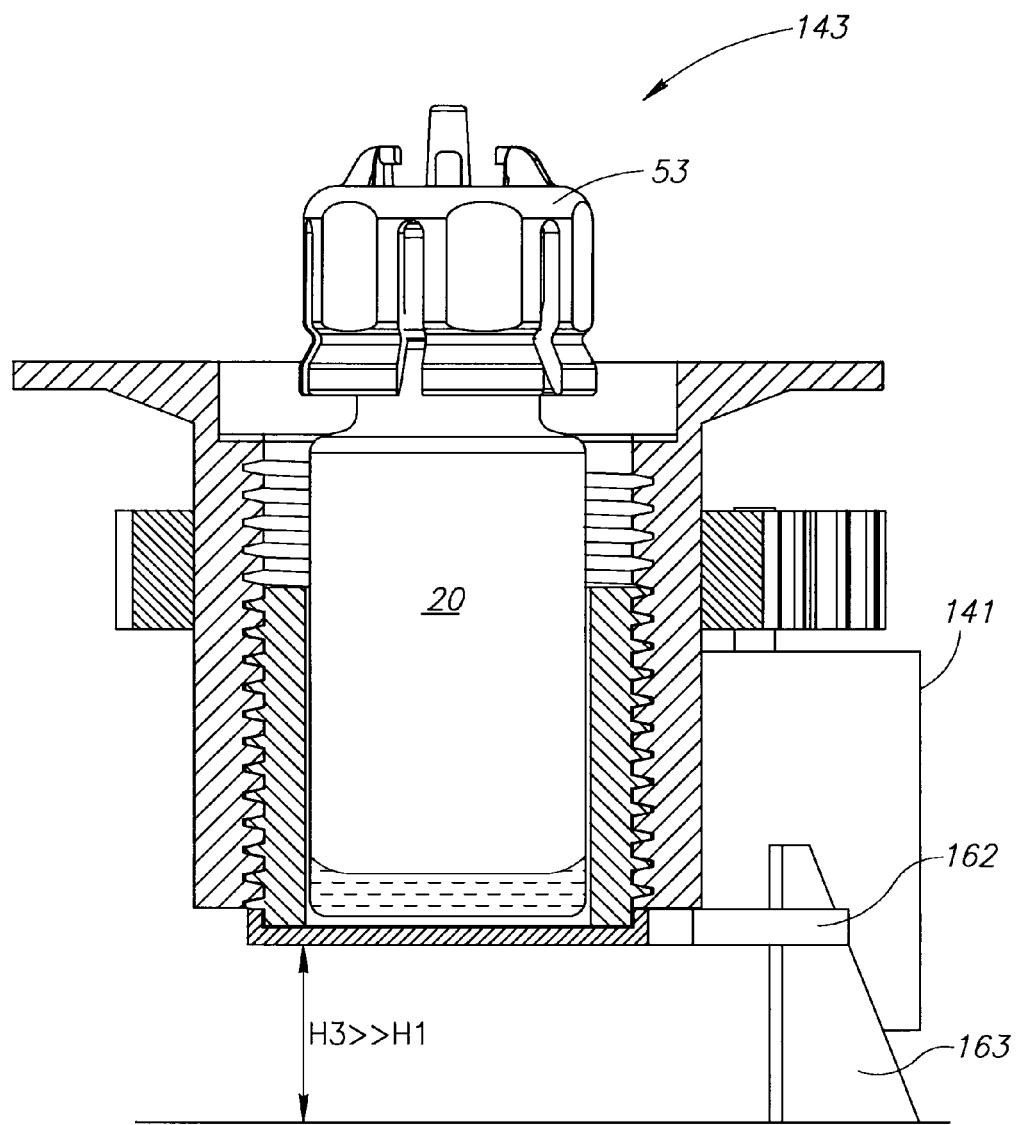
Figure 16:
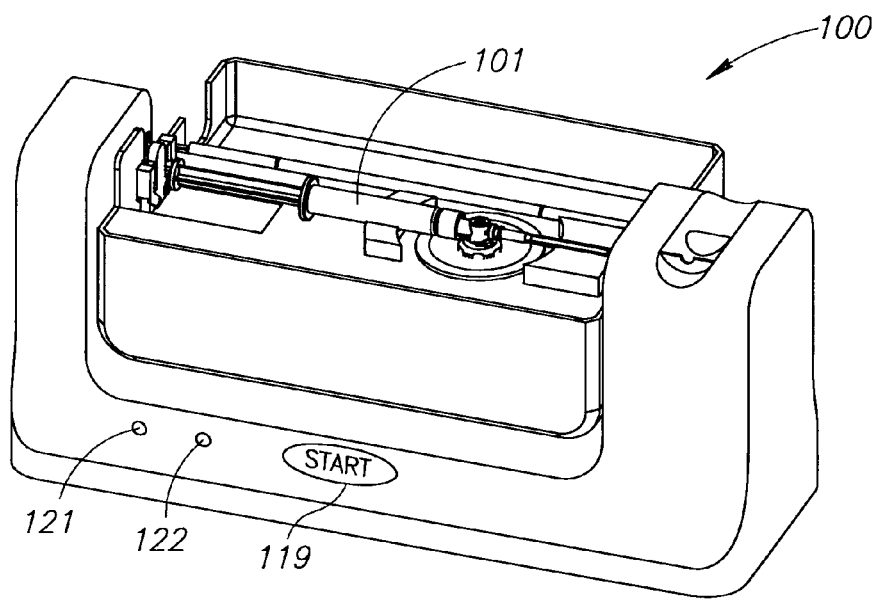
FIG. 16 is a pictorial representation of the automatic liquid drug preparation apparatus showing insertion of a preparatory assemblage.
Figure 17:
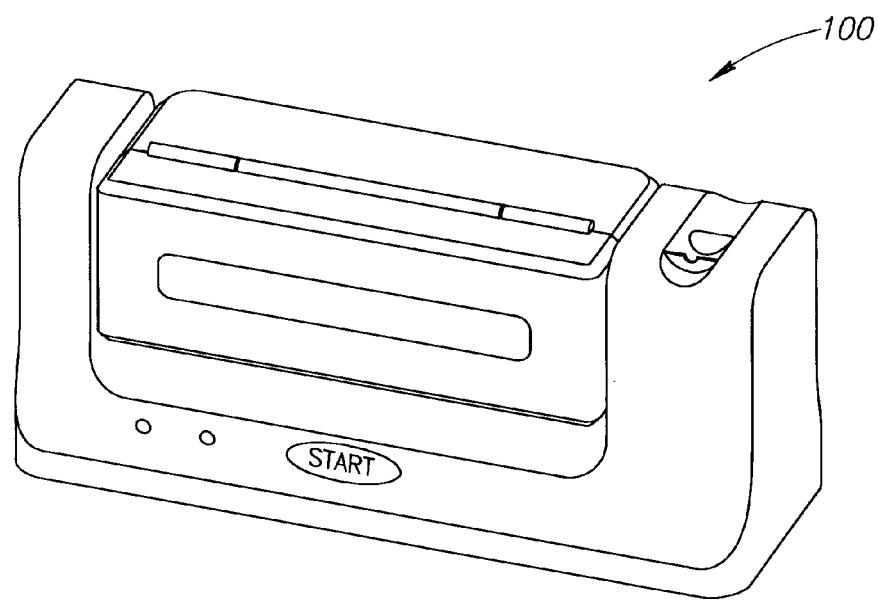
FIG. 17 is a pictorial representation of the automatic liquid drug preparation apparatus showing horizontal positioning of its cradle for injection of diluent into the vial.

FIGS. 15A to 15C show the vial adapter release mechanism 143 includes a cylindrical drive member 157 having an internal screw thread 158 and an open topped upright cylindrical vial holder 159 with an external screw thread 161 engaging the internal screw thread 158. The vial holder 159 includes an outwardly directed slotted protrusion 162 engaging an upright stopper 163 mounted on the cradle's bottom surface 107A whereby the vial holder 159 is linearly displaceable with respect to the annular member 157 on rotation of same by the motor 141. FIG. 15A shows the vial holder 159 at its lowermost position for enabling insertion of a vial 20 thereinto. FIG. 15B shows the vial holder 159 on rotation of the vial adapter gripper 142 to release the vial adapter 53 from the fluid control device 30. FIG. 15C shows the vial holder 159 at its uppermost position for raising the vial adapter 53 for assisting a user to remove the vial adapter 53 and its attached spent vial 20 from the cradle 107.

Operation of the automatic liquid drug preparation apparatus 100 is now described with reference to FIGS. 16 to 24.

The user closes the cover 109 and presses the START pushbutton 119. The controller 114 issues a user indication to indicate the initiation of a homing procedure or the cover 109 is not fully closed thereby preventing initiation of the homing procedure. Suitable user indications include, for example, flashing the green LED 121 for indicating the beginning of a homing procedure, flashing the red LED 122 for indicating an error condition, and the like. In the homing procedure, the controller 114 homes the syringe drive unit 116, the cradle drive unit 117 and the vial adapter release unit 118 to their home positions. The plunger drive member 116 is in its remotest position relative to the end piece 106B. The cradle 107 is in its upward position. The vial adapter release mechanism 143 is in its lowermost position.

The user prepares a preparatory assemblage 101, opens the cover 109, inserts the preparatory assemblage 101 in the cradle 107 (see FIG. 16), closes the cover 109, sets the dosage selector 123, and presses the START pushbutton 119. The controller 114 issues a user indication to indicate the initiation of a mixing procedure or the cover 109 is not fully closed thereby preventing initiation of the mixing procedure. The cradle drive unit 117 rotates the cradle 107 through a near 90° with respect to its initial upright position to a near horizontal position for injecting diluent into the vial 20 for minimizing foaming (see FIG. 17). The syringe drive unit 116 urges the carriage 132 forward whereupon the flipper arrangement 133 engages the plunger head 14. The flipper arrangement 133 does not snap fit onto the plunger head 14 immediately but rather urges the plunger head 14 towards the syringe's end wall 12 for injecting diluent into the vial 20. The syringe drive unit 116 initially issues a series of fast pulses to the motor 116 to overcome the plunger tip 16's static friction and then slows the pulse rate to the motor 116 to avoid injecting diluent into the vial 20 too quickly. The near horizontal position of the cradle 107 ensures that diluent droplets run down the barrel 11's inside surface instead dropping directly onto the medicament which tends to cause foaming particularly in the case of a powder medicament.

The syringe drive unit 116 continues to issue pulses to the motor 116 until the plunger tip 16 abuts against the inside surface of the syringe's end wall 12 on injection of the syringe's entire diluent contents into the vial 20. The syringe drive unit 116 senses the carriage 132 has stopped and sets the syringe linear encoder 136 to zero for enabling accurate determination of the volume of the syringe's liquid contents on aspiration of liquid contents thereinto from the vial 20. The flippers 147 are urged outwardly open on abutment of the plunger tip 16 against the syringe's end wall 12 whereupon they snap fit onto the plunger head 14 for engaging same.

Figure 18:
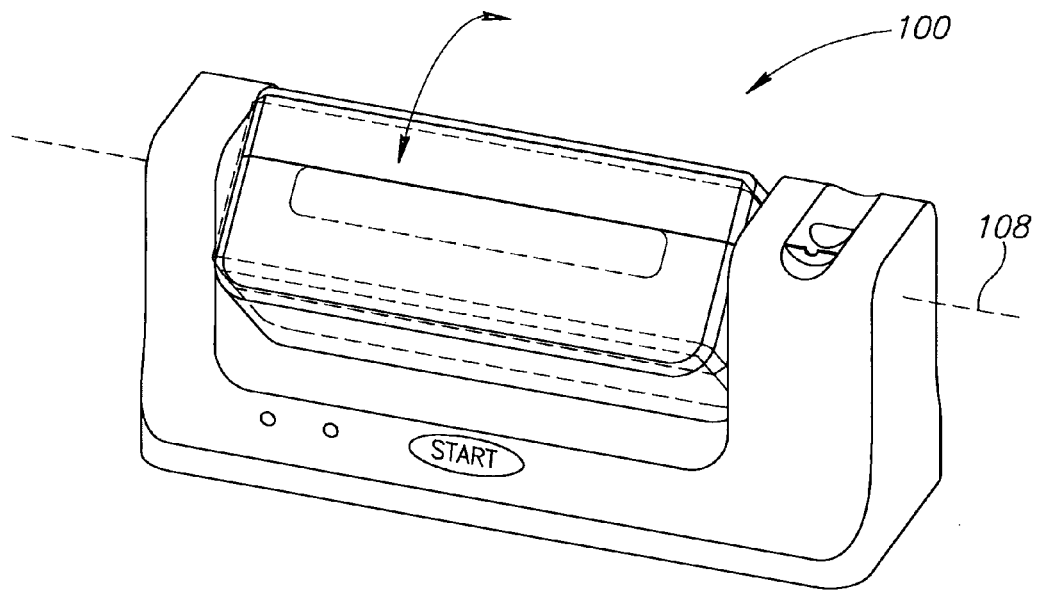
FIG. 18 is a pictorial representation of the automatic liquid drug preparation apparatus showing agitation of its cradle for mixing diluent with the medicament.
Figure 19:
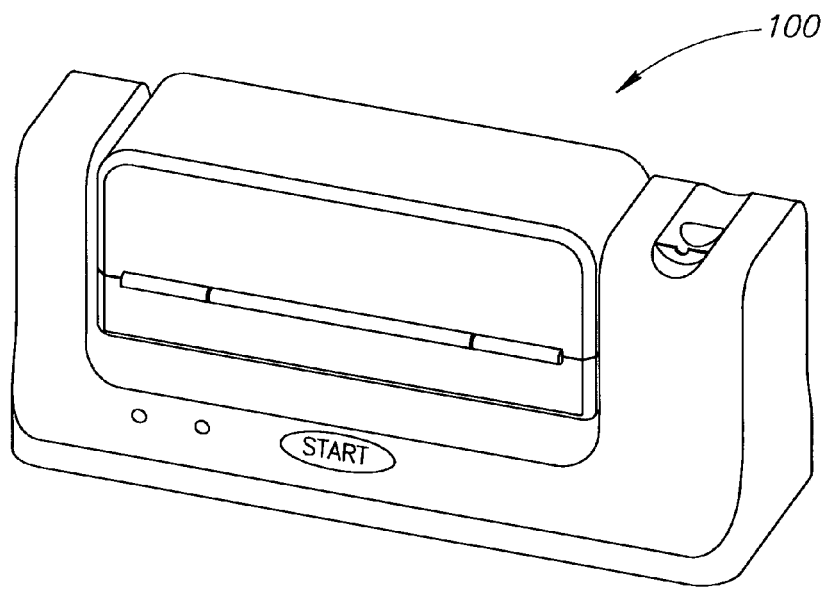
FIG. 19 is a pictorial representation of the automatic liquid drug preparation apparatus showing inversion of its cradle for executing a trapped air displacement procedure and aspirating liquid drug into its syringe.
Figure 20:
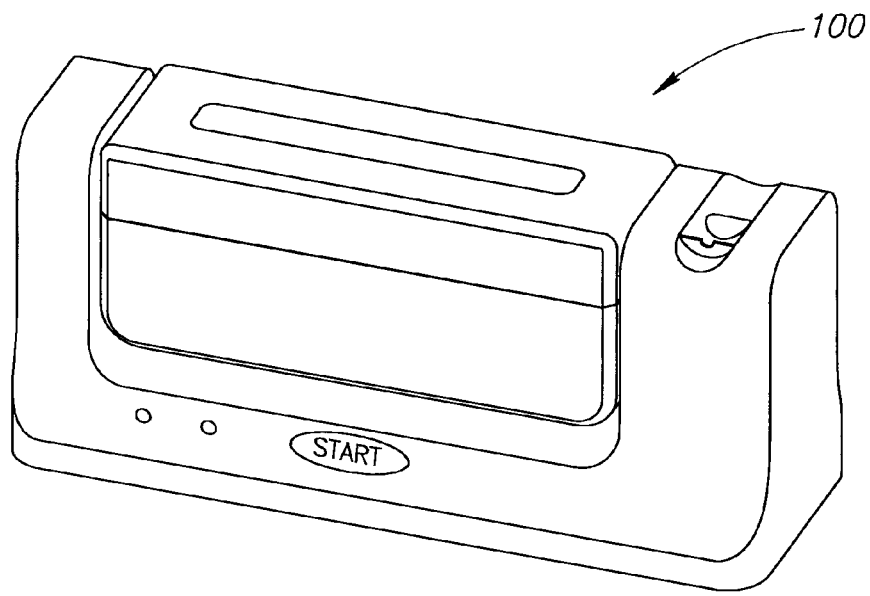
FIG. 20 is a pictorial representation of the automatic liquid drug preparation apparatus showing restoration of its cradle to its original upright position.

The cradle drive unit 117 returns the cradle 107 to its original upright position and begins to reciprocate the cradle 107 back and forth through about an agitation angle of from about ±30° to about ±70° relative to the original upright position for mixing the diluent with the medicament to form liquid drug contents (see FIG. 18). The agitated liquid drug contents are allowed to settle for about 30 seconds. The cradle drive unit 117 rotates the cradle 107 to an inverted position (see FIG. 19) and allows the liquid drug contents to settle for about 10 seconds. In this position, the plunger tip 16 abuts against the inside surface of the syringe's end wall 12 such that the syringe 10 itself does not contain any air. However, some air is often entrapped in the preparatory assemblage's mixing flow path 67 between the syringe 10 and the vial 20. The controller 114 initiates a trapped air displacement procedure to displace as much of this entrapped air as possible to the vial 20 which is inverted above the syringe 10. Thus, the liquid drug contents in the liquid drug assemblage 102 is near air free as possible but may still possibly contain minute air bubbles having an accumulated air bubble volume of a few micro liters.

The trapped air displacement procedure involves the repeated transfer of liquid drug contents between the syringe 10 and the vial 20. The trapped air displacement procedure typically involves two stages: an initial stage of a few long reciprocations, say, about, five, and a subsequent stage of more short reciprocations, say, between ten and twenty. In the case of a 1 ml syringe, each long reciprocation has an about 4.5 mm long stroke and takes about 2.5 seconds and each short reciprocation has an about 2.5 mm long stroke and takes about 1.5 seconds. The long reciprocations typically transfer about a third of a preparatory assemblage 101's liquid drug contents between the syringe 10 and the vial 20 for fragmenting any air bubbles trapped in its mixing flow path 67 into smaller air bubbles. Thereafter, the short reciprocations may further fragment the small bubbles into smaller bubbles but more importantly they inject the liquid drug contents entraining the air bubbles into the vial 20 with sufficient force that at least some of the air bubbles are sufficiently far from the syringe 10 so as not to be re-aspirated back thereinto in the next aspiration of liquid drug contents. Such escaped air bubbles are then free to float to the top of the vial 20's liquid drug contents to add to its existing air volume thereby progressively reducing the accumulated air bubble volume being entrained in the liquid drug contents being transferred between the syringe 10 and the vial 20. The liquid drug contents are allowed to settle for about 30 seconds after the trapped air displacement procedure before the syringe drive unit 116 aspirates a predetermined dosage of liquid drug into the syringe 10 according to the dosage selector 123's setting.

Figure 21:
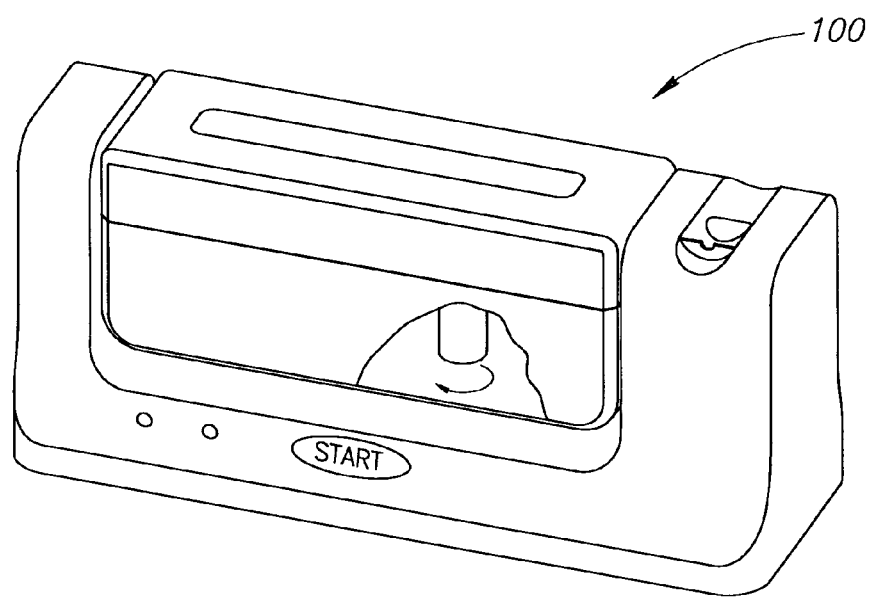
FIG. 21 is a pictorial representation of the automatic liquid drug preparation apparatus showing release of its vial adapter with its attached spent vial from the body member.
Figure 22:
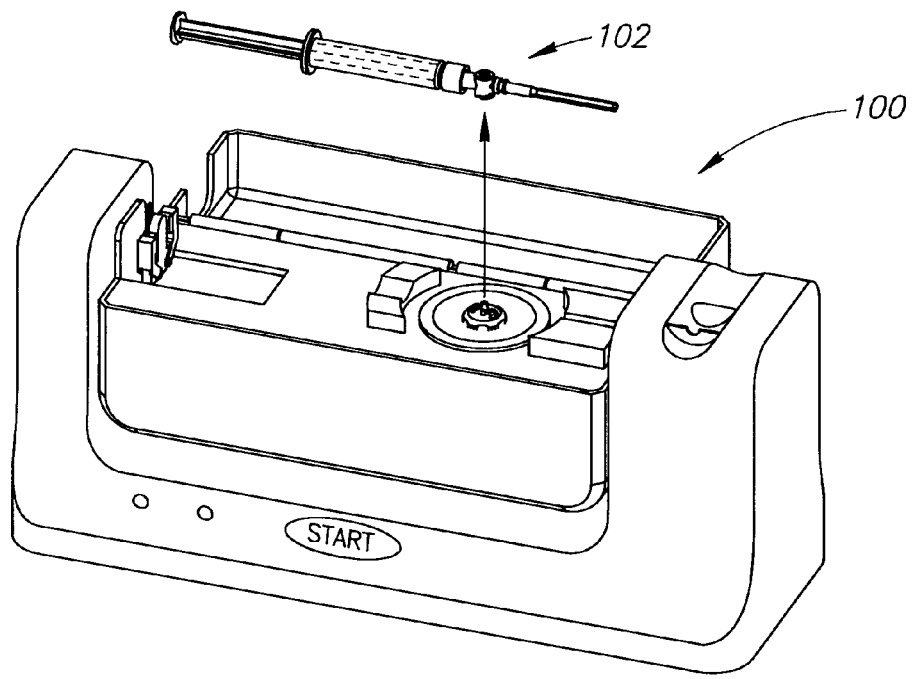
FIG. 22 is a pictorial representation of the automatic liquid drug preparation apparatus with its cover open for enabling manual removal of the liquid drug assemblage.
Figure 23:
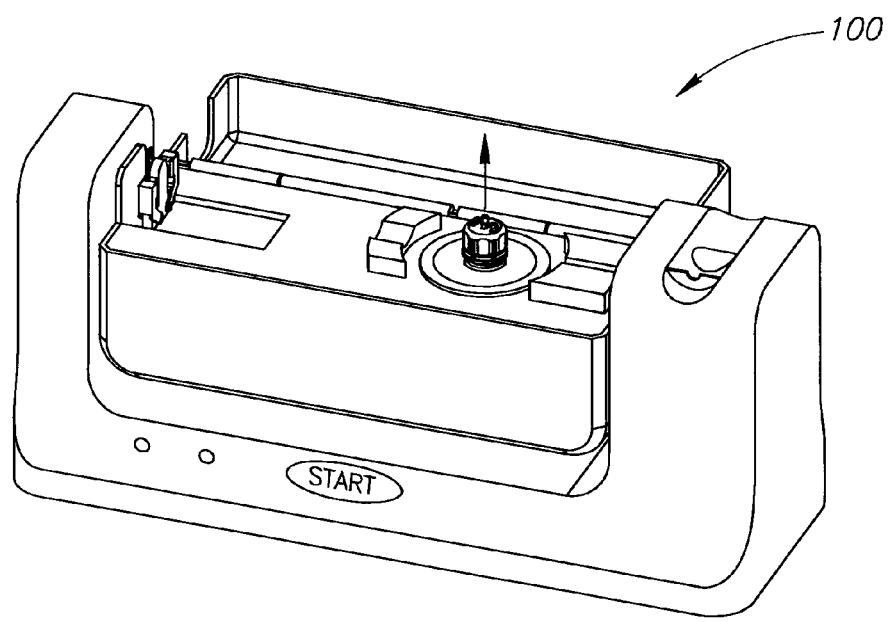
FIG. 23 is a pictorial representation of the automatic liquid drug preparation apparatus showing the vial adapter lifted upwards for assisting its manual removal for disposal purposes.
Figure 24:
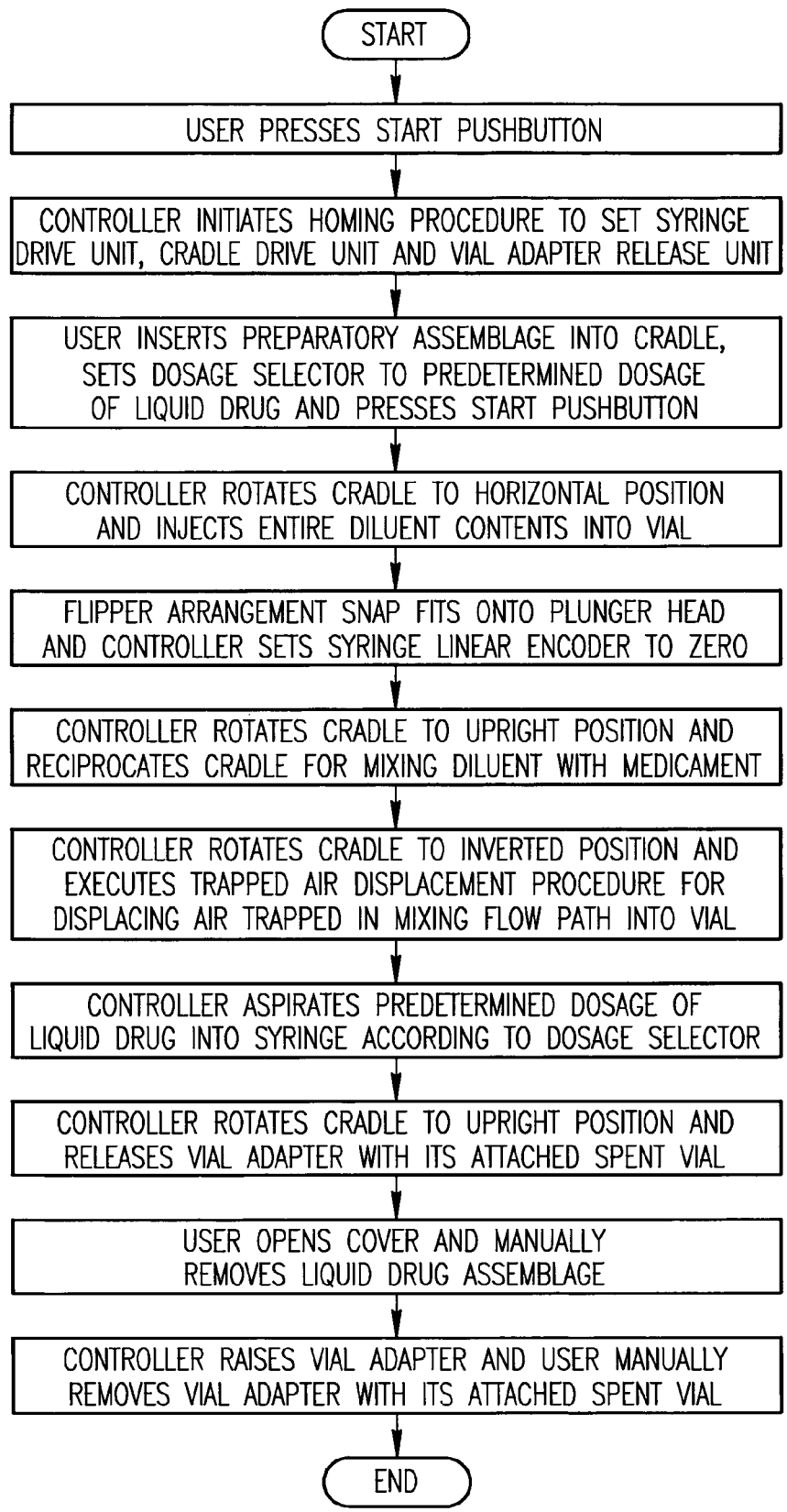
FIG. 24 is a flow diagram of the operation of the automatic liquid drug preparation apparatus.

The cradle drive unit 117 rotates the cradle 107 to its original upright position (see FIG. 20) and the vial adapter release unit 118 rotates the vial adapter gripper 142 through about 120° in a counter clockwise direction to initially engage the vial adapter 53 and then release the vial adapter 53 with its attached spent vial 20 from the body member 31 (see FIG. 21).

The controller 114 provides a user indication to the user that the liquid drug assemblage 102 is ready for removal. The user opens the cover 109 and manually removes the liquid drug assemblage 102 for administration (see FIG. 22). The vial adapter release unit 118 waits about 30 seconds before rotating the drive member 157 to cause the vial holder 159 to raise the vial adapter 53 (see FIG. 23) thereby enabling the user to readily manually remove the vial adapter 53 and its attached spent vial 20. As described hereinabove in connection with a manually prepared liquid drug assemblage, some freshly mixed liquid drug contents start bubbling in the liquid drug assemblage 102 due to a chemical reaction between a medicament and a diluent including an active chemical component, thereby re-introducing air bubbles into the liquid drug contents.

Figure 25:
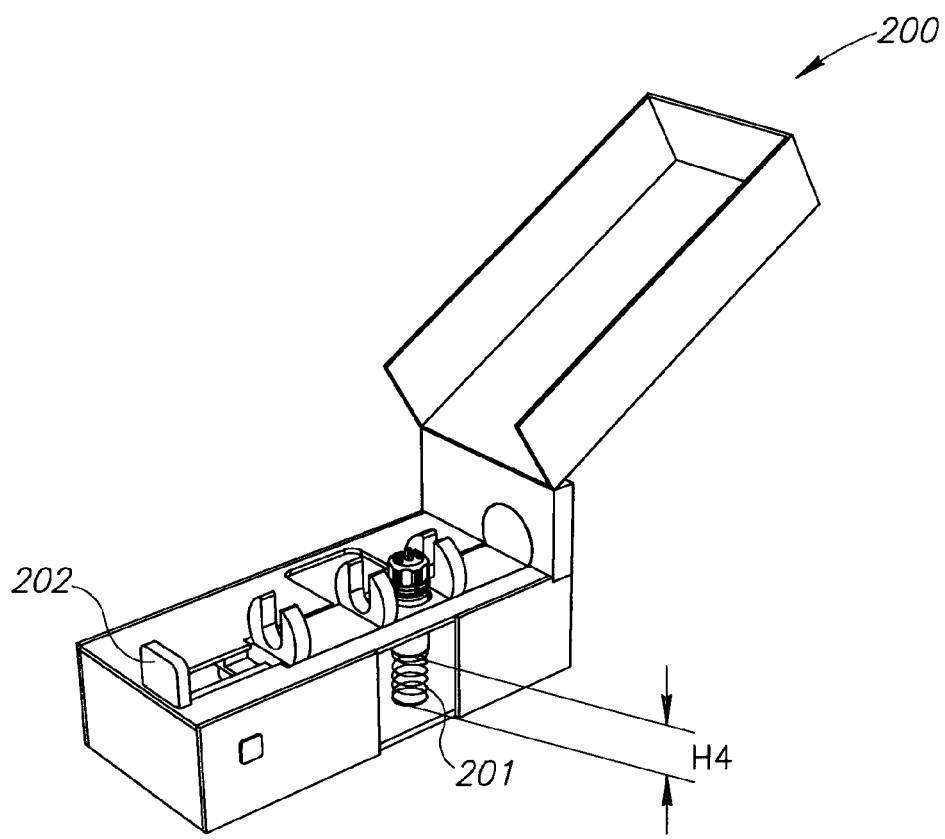
FIG. 25 is a pictorial representation of an alternative embodiment of automatic liquid drug preparation apparatus.
Figure 26:
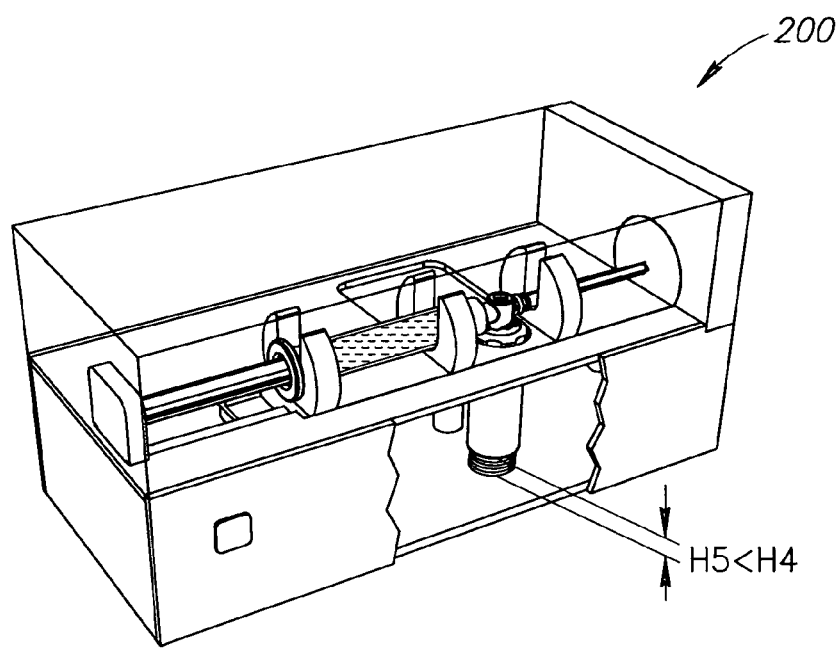
FIG. 26 is a partially cut away pictorial representation of FIG. 25's automatic liquid drug preparation apparatus.

FIGS. 25 and 26 show an alternative automatic liquid drug preparation apparatus 200 for processing a preparatory assemblage 101 into a liquid drug assemblage 102. The apparatus 200 includes a compression spring 201 for lifting a detached vial adapter and its attached spent vial. The compression spring 201 has a non-compressed height H4 compressed to a compressed height H5<H4 on insertion of a preparatory assemblage 101. Other modifications of the apparatus 200 can include inter alia the use of magnets for ensuring a plunger head driver member 202 engages a preparatory assemblage's plunger head for enabling reciprocation of its plunger, a vial adapter release unit for directly rotate a vial instead of a vial adapter, and the like.

While the invention has been described with respect to a limited number of embodiments, it will be appreciated that many variations, modifications, and other applications of the invention can be made within the scope of the appended claims.

The invention claimed is:

1. Automatic liquid drug preparation apparatus for preparing a predetermined dosage of liquid drug for administration,
the apparatus intended for use with a preparatory assemblage with liquid drug constituents for processing into a liquid drug assemblage with the predetermined dosage, of liquid drug,
the preparatory assemblage including a fluid control device, a vial prefilled with a medicament and having a vial longitudinal axis, and a syringe with a syringe longitudinal axis and having a syringe end wall with an inside surface and a reciprocal plunger with a proximal plunger head and a distal plunger tip, the syringe being pre-filled with diluent for mixing with the medicament,
the fluid control device including a body member having a syringe port for receiving the syringe, a vial adapter having a downward depending skirt with a plurality of upright slits defining flex members for snap fitting onto the vial, and
a drug administration port for administrating the liquid drug,
the vial adapter and the vial attached thereto being detachable from the body member on rotation with respect thereto,
the fluid control device having a mixing flow path between the syringe port and the vial adapter and an administration flow path between the syringe port and the drug administration port,
the apparatus comprising:
(a) a housing;
(b) a cradle for manual insertion of the preparatory assemblage thereinto; and
(c) a controller for controlling the operation of
(i) a motorized syringe drive unit for selectively reciprocating a plunger head drive member engaging the plunger head for reciprocating the plunger relative to the fluid control device for transferring liquid contents between the syringe and the vial when the syringe longitudinal axis is perpendicular to the vial longitudinal axis,
(ii) a motorized cradle drive unit for selectively rotating said cradle with the preparatory assemblage about the syringe longitudinal axis relative to an initial upright position in said housing, and
(iii) a motorized vial adapter release unit for selectively rotating the vial adapter about the vial longitudinal axis relative to the body member for detaching the vial adapter and its attached spent vial from the body member.

2. Apparatus according to claim 1 wherein said controller executes a syringe linear encoder reset procedure to reset a syringe linear encoder for determining the location of the syringe's plunger relative to the syringe's barrel for enabling aspiration of the predetermined dosage of liquid drug.

3. Apparatus according to either claim 1 wherein said controller operates said cradle drive unit to rotate said cradle and the preparatory assemblage to a substantially inverted position and operates said syringe drive unit to execute a trapped air displacement procedure involving the repeated transfer of liquid drug contents between the syringe and the vial for entraining air bubbles initially entrapped in the mixing flow path between the syringe and the vial therewith for fragmenting the air bubbles into smaller air bubbles for being progressively added to the vial's air volume thereby progressively reducing the accumulated air bubble volume in the liquid drug contents.

4. Apparatus according to claim 3 wherein said trapped air displacement procedure includes an initial series of long strokes of the plunger of the syringe and a subsequent series of short strokes of the plunger of the syringe.

5. Apparatus according to claim 1 wherein said controller operates said cradle drive unit for rotating said cradle and the preparatory assemblage through near 90° relative to said upright position to a near horizontal position and operates said syringe drive unit to inject the diluent from the syringe into the vial.

6. Apparatus according to claim 1 and further comprising a hinged cover for covering the preparatory assemblage and a cover safety mechanism for preventing operation of the apparatus on detection said cover is not fully closed.

7. Apparatus according to claim 6 wherein said cover is hinged on said cradle whereby said cradle and said hinged cover are rotatable relative to said housing.

8. Apparatus according to claim 1 wherein said syringe drive unit initially urges said plunger head drive member against the plunger head for displacing the plunger toward the fluid control device whereupon, on abutment of the plunger tip against the syringe's end wall, said plunger head drive member engages the plunger head.

9. Apparatus according to claim 8 wherein said plunger head drive unit is constituted by a flipper arrangement with a pair of flippers biased towards one another whereupon said pair of flippers initially pivot outwards and subsequently snap fit onto the plunger head on abutment of the plunger tip against the syringe's end wall.

10. Apparatus according to claim 1 wherein said vial adapter release unit includes an annular vial adapter gripper for encircling the vial adapter on manual insertion of the preparatory assemblage into said cradle, said vial adapter gripper including at least one flexible leaf spring with an upright section having a radial inwardly protruding tab for insertion into an upright slit of the vial adapter's plurality of upright slits for enabling the detachment of the vial adapter from the body member on rotation of the vial adapter relative to the body member.

11. Apparatus according to claim 1 wherein said vial adapter release unit includes a vial adapter release mechanism for selectively raising the vial adapter and its attached spent vial on detachment of the vial adapter from the body member thereby assisting a user to manually remove the vial adapter and its attached spent vial from said cradle.

12. Apparatus according to claim 11 wherein said vial adapter release mechanism includes a rotatable annular member in screw thread arrangement with an open topped upright cylindrical vial holder linearly displaceable with respect to said annular member on rotation of said annular member.

13. Apparatus according to claim 1 wherein said housing includes a blind bore for insertion of a vial for assisting a user to assemblage a preparatory assemblage.

14. Apparatus according to claim 1 wherein said housing includes a V-shaped opener for assisting a user to remove a needle shield from a liquid drug assemblage including a needle with a needle shield.

* * * * *